US012564426B2

(12) United States Patent
Heuer

(10) Patent No.: US 12,564,426 B2
(45) Date of Patent: Mar. 3, 2026

(54) MODULAR AND TEMPORARILY FIXABLE OSTEOSYNTHESIS DEVICE FOR VERTEBRAE

(71) Applicant: MIMEO MEDICAL GmbH, Filderstadt (DE)

(72) Inventor: Frank Heuer, Filderstadt (DE)

(73) Assignee: MIMEO MEDICAL GmbH, Filderstadt (DE)

( * ) Notice: Subject to any disclaimer, the term of this patent is extended or adjusted under 35 U.S.C. 154(b) by 326 days.

(21) Appl. No.: 18/246,826

(22) PCT Filed: Sep. 28, 2021

(86) PCT No.: PCT/EP2021/076697
§ 371 (c)(1),
(2) Date: Mar. 27, 2023

(87) PCT Pub. No.: WO2022/064070
PCT Pub. Date: Mar. 31, 2022

(65) Prior Publication Data
US 2023/0363798 A1     Nov. 16, 2023

(30) Foreign Application Priority Data
Sep. 28, 2020    (DE) ..................... 10 2020 005 928.7

(51) Int. Cl.
*A61B 17/70*          (2006.01)
(52) U.S. Cl.
CPC ...... *A61B 17/7032* (2013.01); *A61B 17/7037* (2013.01); *A61B 17/7002* (2013.01)

(58) Field of Classification Search
CPC ............ A61B 17/7032; A61B 17/7037; A61L 27/34
See application file for complete search history.

(56) References Cited

U.S. PATENT DOCUMENTS 10,973,554 B2 *   4/2021   Biedermann ...... A61B 17/7032
12,262,921 B2 *   4/2025   Lang .................. A61B 17/7032
(Continued)

FOREIGN PATENT DOCUMENTS

DE       10 2018 102 173       6/2019
EP             2 022 423       2/2009
(Continued)

OTHER PUBLICATIONS

International Search Report with English Translation dated Feb. 2, 2022, for PCT/EP2021/076697, 5 pages.
(Continued)

*Primary Examiner* — Matthew J Lawson
(74) *Attorney, Agent, or Firm* — Nixon & Vanderhye, PC

(57) ABSTRACT
An osteosynthesis device for treating the spine is disclosed including a fork head which is U-shaped in a side view, has two fork legs in the proximal direction with an internal thread, and in which a connecting rod can be received, and a locking element is guided in the internal thread, and the fork head has a spherical head receiving area and is detachably connected to a bone anchor, and the bone anchor is pivotably mounted in the spherical seat of the spherical head receiving area, wherein the fork head has slots which are open in the distal direction at the spherical head receiving area and at least two deflectable legs are thereby formed, and a locking ring mounted at least partially around the spherical head receiving area.

29 Claims, 15 Drawing Sheets

(56)         References Cited

U.S. PATENT DOCUMENTS

| 2006/0200128 | A1  | 9/2006  | Mueller |  |
|---|---|---|---|---|
| 2009/0149887 | A1* | 6/2009  | Schlaepfer | A61B 17/7091 606/301 |
| 2012/0179209 | A1* | 7/2012  | Biedermann | A61B 17/7037 606/279 |
| 2019/0192192 | A1* | 6/2019  | Biedermann | A61B 17/7032 |
| 2019/0274737 | A1* | 9/2019  | Biedermann | A61B 17/7037 |
| 2020/0121367 | A1  | 4/2020  | Biedermann |  |
| 2021/0369315 | A1* | 12/2021 | Heuer | A61B 17/7037 |
| 2022/0330988 | A1* | 10/2022 | Biedermann | A61B 17/7082 |
| 2023/0000527 | A1* | 1/2023  | Biedermann | A61B 17/7038 |

FOREIGN PATENT DOCUMENTS

| EP | 3 287 088 | 2/2018 |
|---|---|---|
| EP | 3 437 576 | 2/2019 |

OTHER PUBLICATIONS

Written Opinion of the ISA dated Feb. 2, 2022, for PCT/EP2021/076697, 7 pages.

* cited by examiner $$SP1 = (D15 - D19) / 2$$

MODULAR AND TEMPORARILY FIXABLE OSTEOSYNTHESIS DEVICE FOR VERTEBRAE

CROSS REFERENCE TO RELATED APPLICATIONS

The present application is a National Phase of International Application Number PCT/EP2021/076697 filed Sep. 28, 2021, which designated the U.S. and claims priority benefits from German Patent Application Number DE 10 2020 005 928.7 filed Sep. 28, 2020, the entire contents of each of which are hereby incorporated by reference.

STATE OF THE ART

In the state of the art, various osteosynthesis devices for the treatment of the spine, such as pedicle screws, are known. Such osteosynthesis devices are used to correct spinal deformities or stabilize fractures by inserting and securing the osteosynthesis devices into the vertebral bone and then connecting them via longitudinal rods, or so-called connecting rods, to fix the vertebrae in a desired position. The longitudinal rods are mounted on the osteosynthesis devices with the help of grub screws and fixed in a slip-resistant manner. Preferably, pedicle screws are used as osteosynthesis devices, which have a bone anchor that can be pivoted polyaxially with a fork head and is angularly stable when the grub screw is fixed. Bone screws with a ball head are preferably used as bone anchors. Osteosynthesis devices with bone anchor and fork head are usually mounted in such a way that the bone anchor is inserted into the fork head from the proximal side and the bone anchor shaft is inserted through the distal opening of the fork head. This only works if the outer diameter of the bone anchor shaft is smaller than the ball head diameter of the bone anchor and the outer diameter of the bone anchor shaft is smaller than the diameter of the distal opening of the fork head. Mounting is complicated if the outer diameter of the bone anchor shaft is larger than the opening diameter of the fork head and/or the ball diameter of the bone anchor.

In the state of the art, for example, a pedicle screw design is known from US20060200128A1 or US2020121367A1, in which the fork head can be mounted from the distal side with a bone anchor. In this case, the fork head is configured in several parts and has a kind of grip chuck at the distal fork head area. Three or more components are often necessary. A multi-part construction of a bone anchor is disadvantageous in terms of mechanical stability and maximum load capacity. Overloading can lead to disassembly and thus to premature implant failure. Therefore, a design with as few components as possible would be desirable, as it also reduces the number of possible errors in manufacturing.

Furthermore, pedicle anchors (DE102018102173B3) are known from the state of the art that can be temporarily locked and thus allow for a wider range of applications in the treatment of spinal instabilities. Such an arrangement is technologically and from a manufacturing point of view complex and cost-intensive. It is therefore desirable to provide as few components as possible, to implement temporary clampability, to reduce the mounting steps and at the same time to optimize the manufacturing costs.

REPRESENTATION OF THE INVENTION

The invention relates to an osteosynthesis device, in particular a polyaxial pedicle screw, with a bone anchor having a head and with a fork head which is U-shaped in a side view, with a locking ring attached thereto and a receiving opening located on the fork head for a connecting rod, in particular a correction rod, and a locking element guided in the fork head. Bone screws that can be screwed to a bone are preferably used as bone anchors. However, hooks, clamps, nails and other types of bone anchors can also be used. The essential features of the bone anchor are a ball-like head, a neck region and a region which can be anchored or fixed in or to the bone. In this patent application, the fork head is mainly intended to be discussed, and bone anchor is intended to be understood as all possible elements that can be connected to a bone.

An essential feature of the fork head is that the spherical head receiving area has distally open slots and thus at least one deflectable leg is formed. The legs form the spherical seat for the bone anchor head towards the inside. When the legs are deflected outwards, they expose the spherical head of the bone anchor. When the legs are inwardly deflected, they generate a compressive force on the ball head of the bone anchor and create a clamping. The legs have a cone section on the outside through which the compression force can be introduced. Furthermore, the outer contour has a cylindrical area which is used to set a non-force applied form fit between the locking ring and the spherical head receiving area of the fork head. The spherical head receiving area and the locking ring have regularly repeating recesses at the form fit, so that this form fit can be deactivated when the locking ring is rotated.

Furthermore, the osteosynthesis device has a locking ring which is at least partially mounted around the spherical head receiving area of the fork head, so that the locking ring can be rotated about a central axis relative to the fork head. A first rotational position (R1) can be set in which the spherical head receiving area can be deflected radially outwards with its legs so that the bone anchor can be removed and/or inserted, and a second rotational position (R2) can be set in which the spherical head receiving area is blocked in its deflectability with its legs so that the bone anchor is held stationary but pivotable. By rotating the locking ring to the R2 rotational position, a form fit is provided between the maximum outer cylindrical contour of the fork head and the smallest inner cylindrical contour of the locking ring. This form fit prevents any spreading of the spherical head receiving area and thus the bone anchor is mounted in the fork head so that it cannot be lost but can be moved. Twisting in another direction (R1) reopens this form fit and the spherical head receiving area is deformable so that the bone anchor can be removed.

Due to this very positive feature, the fork head is adapted to accommodate different rod diameters. If the locking ring is in the R1-rotational position, the bone anchor can be mounted relatively easily with the fork head by placing or pressing on the components in this advantageous arrangement. The bone anchor can also be removed again using an auxiliary device, such as a release instrument. Thus, the osteosynthesis device according to the invention can be configured modularly by the user and can be assembled in the operating room later than the time of manufacture. This makes it possible, for example, for the bone anchor to be anchored or screwed into the bone individually first, and then the fork head to be attached to the already implanted bone anchor with the locking ring. This has the advantage that after implanting the bone anchor, the surgeon has much more space and a better view in the operating field compared to the otherwise fully implanted pedicle screws. After assembly, the locking ring is brought into the rotational position R2 and the polyaxial pedicle screw can be implanted as usual.

This has the advantage that, on the one hand, larger bone anchors, i.e. bone anchors with a larger outer diameter than the distal inner diameter of the fork head, can be mounted. On the other hand, the bone anchor portfolio can be minimized, as the user can combine fork head and bone anchor during surgery instead of using a prefabricated oversized portfolio. Such a portfolio must be kept in stock by the user and thus significantly more capital is tied up than would be required by the modular version according to the invention.

The rotation of the locking ring is usually done with an instrument, which has been skipped here to simplify the illustrations. This instrument holds both components in an H1 position and allows rotation (e.g. R1 to R2 or vice versa) of the two components in respect to each other. Optimally, the osteosynthesis device is released from the instrument only when the rotational position R2 is set, so that the osteosynthesis device is properly mounted for the application.

According to the preferred embodiment, it is also possible to initiate the clamping effect via a projection or a proximal contact position on the outer wall of the locking ring without the presence of the connecting rod or the grub screw. Since this is not a final clamping with an inserted connecting rod, this type of clamping is called temporary clamping. With temporary clamping, it is possible for the user to convert a polyaxial screw to a monoaxial screw in a desired angular position during surgery. This means that all rotational degrees of freedom of a polyaxial screw are temporarily locked. The screw behaves monoaxially. This allows the user to manipulate the vertebra to be treated both translationally and rotationally until he inserts a connecting rod in the desired end position and fixes it with the grub screw. Such correction movements are not possible with a polyaxial screw, since a correction movement initiated from the outside by the patient results in a free movement of the polyaxial spherical joint and is therefore not passed on to the vertebra. This only works with deactivated rotational degrees of freedom in the ball joint, i.e. temporarily clamped.

Regardless of the temporary clamping, after implantation of the osteosynthesis device into the bone, a connecting rod must be inserted and the osteosynthesis device must be finally fixed in all degrees of freedom with the help of a locking element. This is done by tightening the locking element. When the locking element is tightened, an axial compression force is transmitted from the locking element to the connecting rod, which presses on the rod bearing points of the locking ring and generates a relative movement of the locking ring further distally, so that the spherical head receiving area is compressed by the locking ring via a paired conical connection in such a way that the bone anchor is clamped angularly stable in the spherical seat. Optimally, two or more osteosynthesis devices are connected to each other with the help of a connecting rod.

A circumferential groove with a hook-like profile is provided at the proximal fork head area, which provides a rear grip for an instrument. Alternatively, differently configured groove profiles or other retaining features such as openings are possible, which provide a rear grip for an instrument.

At the proximal end of the fork head, there may be additional and detachable sections with a thread area that allow repositioning of the connecting rod. It is also possible to have a sleeve-like access formed by two longer legs, as used for minimally invasive access. In this case, the detachable leg extensions can optionally be connected to each other at the proximal end. Detachable connection means, for example, predetermined breaking points which are suitable for removing the extensions after the connecting rod has been finally fixed.

All metallic alloys that are known and accepted as orthopedic implant materials are suitable as materials. These include, for example, titanium, cobalt-chromium and stainless steel alloys. If the conventional production of the fork head and the locking ring is not possible or only possible with the highest technological effort, additive manufacturing is the method of choice. Thus, the fork head and/or the locking ring can be built in one piece. Additive manufacturing of metallic alloys, also known as 3D printing, uses the laser or electron beam melting process.

The long-term success of a 3D-printed implant is highly dependent on its post-treatment. Targeted heat treatment (e.g. HIP—hot isostatic pressing) and surface treatment are enormously important. There is relevant literature available on this subject, which explains the interrelationships of the post-treatments. Due to the poorly accessible and fine mechanical features, a grinding and sandblasting process is not effective. Here, a corresponding reduction of the surface roughness can be achieved with the help of chemical etching, which can optionally be supported by galvanic voltage and/or mechanical stimulation. The object is to free the components from incompletely welded particles, as tensile stresses occur here and micro-notches caused by the incompletely welded particles can result in a weakening of the fatigue strength.

Further features, advantages and details of the invention are apparent from the claims and the drawings and the following description of preferred embodiments of the osteosynthesis screw according to the invention.

DESCRIPTION OF THE PREFERRED EMBODIMENTS

Figure 1:
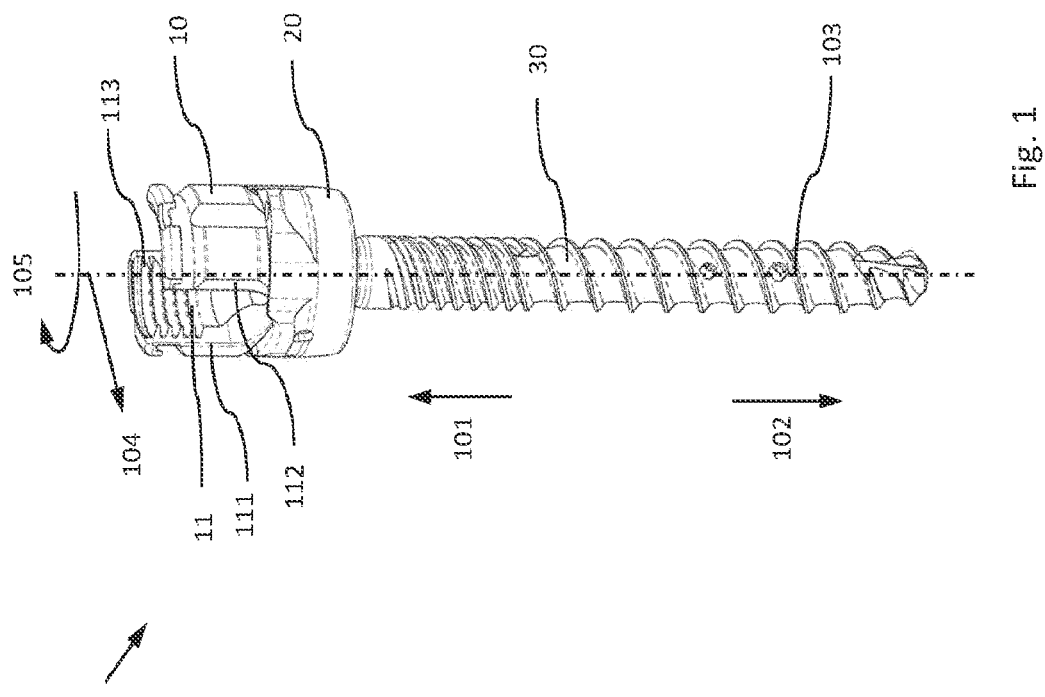
FIG. 1 is an oblique view of the osteosynthesis devices according to the invention.

An osteosynthesis device (1) for the treatment of the spine is disclosed, wherein more than one osteosynthesis device (1) is used to connect one or more vertebrae with each other by means of connecting rods (40) and thus to stabilize the spine. For the osteosynthesis device (1), in particular for the fork head (10), space-allocating coordinate references are defined, such as the proximal direction (101), the distal propagation (102) is defined along a central axis (103). The radial spread (104) is defined as extending outwards from the central axis (103) and the circumferential spread (105) is defined by a constant radius and a variable circumferential angle (FIG. 1).

Figures 2A, 2B, 2C:
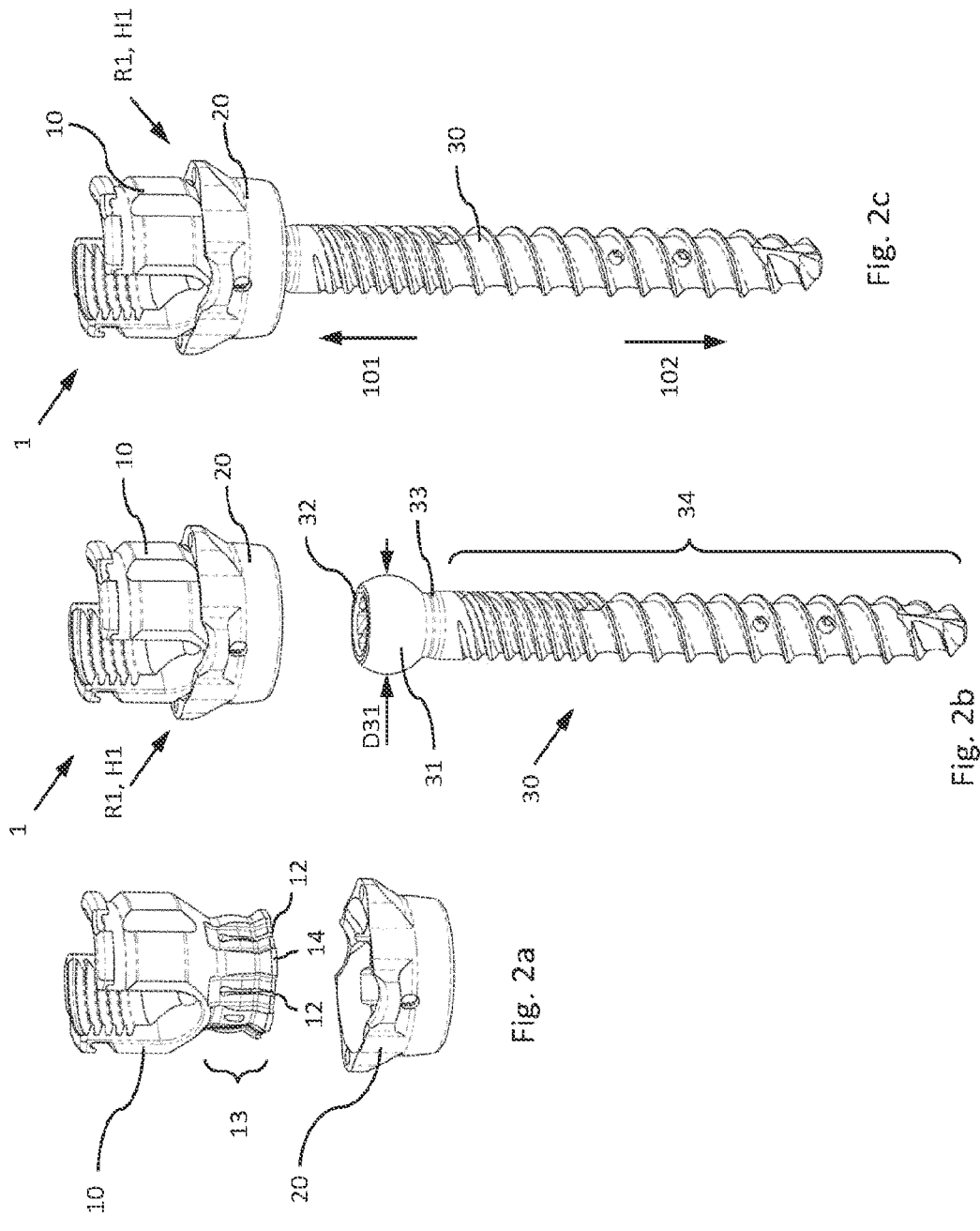
FIG. 2a is an exploded view of an osteosynthesis device according to the invention comprising a fork head and a locking ring.
FIGS. 2b and 2c are the assembly with a bone anchor.

The osteosynthesis device (1) has a fork head (10) which is U-shaped in side view and has two fork legs (111, 112) in the proximal direction (101) with an internal thread (113), in which a connecting rod (40) can be inserted, and in which a locking element or grub screw (60) is guided in the internal thread (113). and the fork head (10) is detachably connected to a bone anchor (30) (FIG. 1, FIGS. 2*b* and 2*c*), and the bone anchor (30) is pivotably mounted in the spherical head receiving area (13) of the fork head (10), wherein the fork head (10) has slots (12) which are open in the distal direction at the spherical head receiving area (13) and at least one deflectable leg (14) is thereby formed (FIG. 2*a*).

The bone anchor (30) has a head (31), a tool attachment point (32), a neck area (33) and optionally a bone thread (34). The head (31) is characterized by a spherical outer surface, which can be determined by a diameter D31 (FIG. 2*b*).

Figures 3A, 3B:
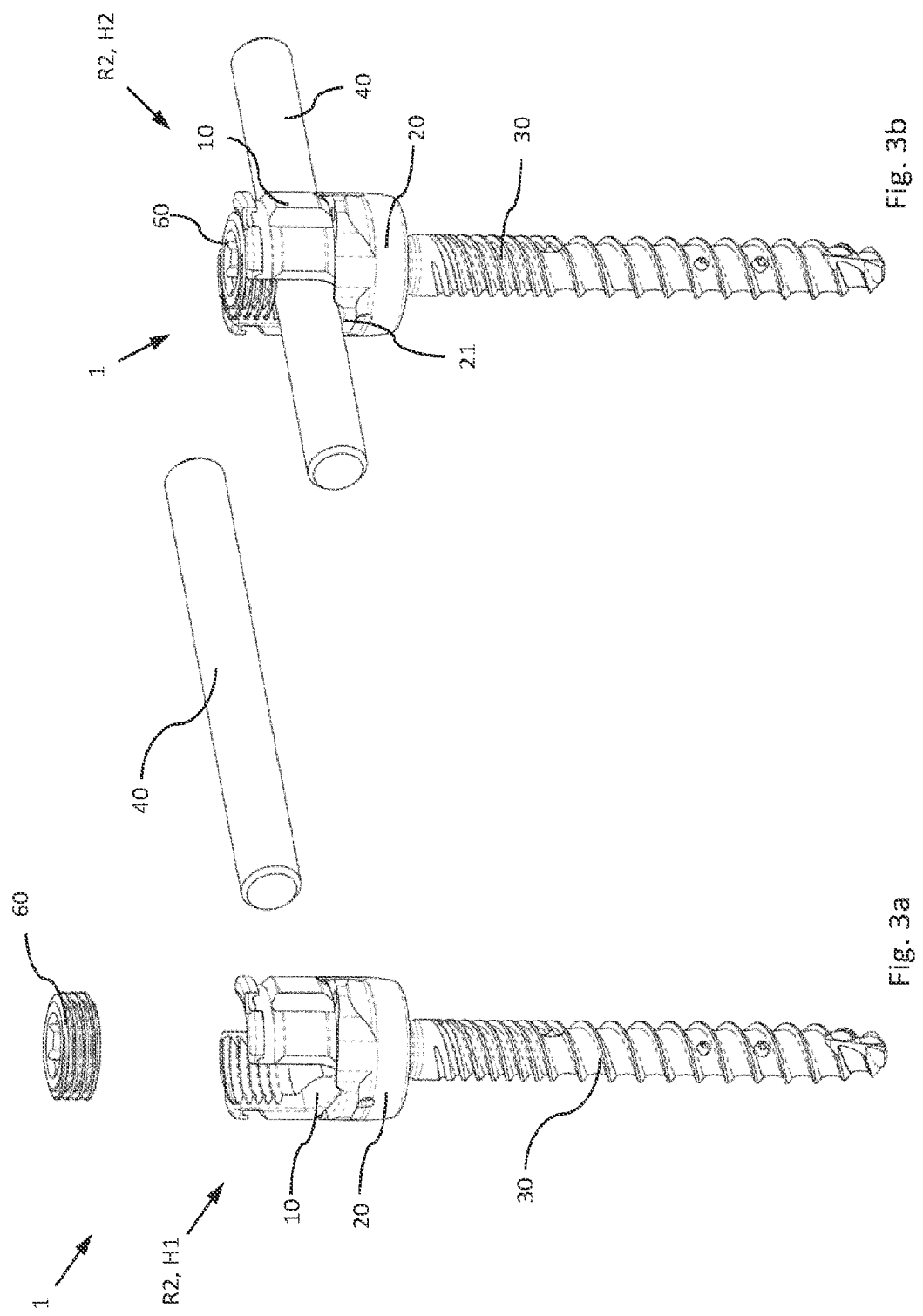
FIG. 3a is an oblique view of the finally assembled osteosynthesis device according to the invention and the insertion of a connecting rod and a locking element.
FIG. 3b is the osteosynthesis device according to the invention finally fixed in an angle-stable manner with the locking element.

Furthermore, the osteosynthesis device (1) has a locking ring (20) which is at least partially mounted around the spherical head receiving area (13) so that the locking ring (20) can be rotated about a central axis (103) relative to the fork head (10) (FIGS. 2*c* and 3*a*). A first rotational position (R1) can be set in which the spherical head receiving area (13) can be deflected (57) with its legs (14) radially outwards so that the bone anchor (30) can be removed and/or inserted, and a second rotational position (R2) can be set in which the spherical head receiving area (13) is blocked (58) in its deflectability with its legs (14) so that the bone anchor (30) is held stationary but pivotable. The exact functionality of the rotational positions and positions of the locking ring are explained in the following figures.

Grub screws (60), for example, can be used as locking elements (FIGS. 3*a* and 3*b*). Usually, they have a tool attachment point, an outer thread and a distal contact surface, which is in contact with the connecting rod (40) in the assembled state. Preferably, the outer thread of the grub screw has an undercut so that the two fork head legs (111 and 112) do not deform radially outwards when the grub screws are tightened.

FIG. 3*b* shows the configuration of the osteosynthesis device (1) when it is finally fixed with a connecting rod. When the locking element (60) is tightened, an axial compression force is transmitted from the locking element (60) to the connecting rod (40), which presses on the rod bearing points (21) of the locking ring (20) and generates a relative movement of the locking ring (20) further distally, so that the spherical head receiving area (13) is compressed by the locking ring (20) in such a way that the bone anchor (30) is clamped in the spherical seat (15) in an angularly stable manner.

Figures 4A, 4B:
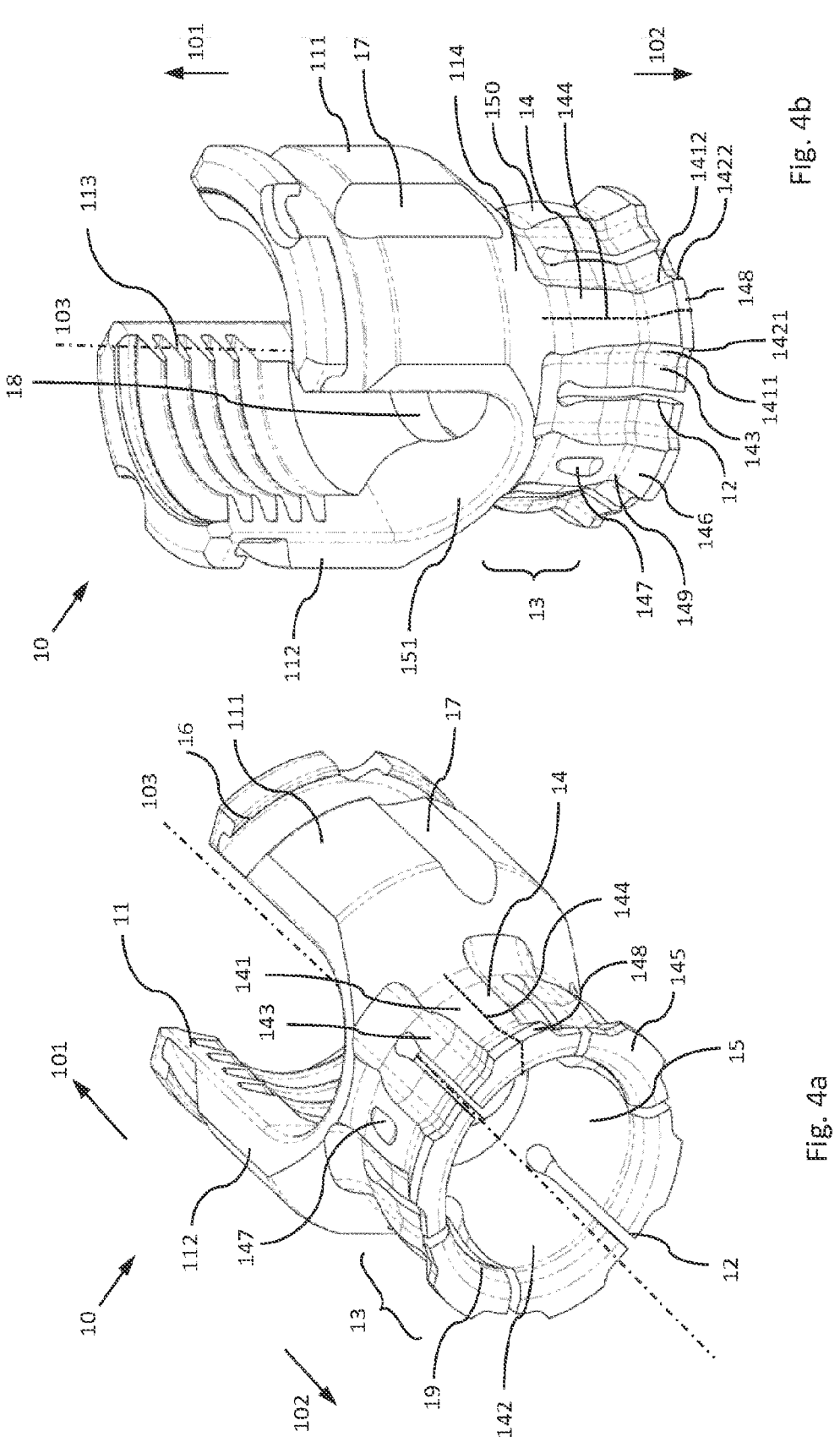
FIG. 4a is the fork head components in an oblique view.
FIG. 4b is in an alternative oblique view.

FIGS. 4*a* and 4*b* show the structure of the preferred embodiment of the fork head (10). It can be seen that legs (14) separated by slots are formed at the distal end (102) of the fork head. The legs (14) have an outer contour (141) which forms the spherical head receiving area (13). Furthermore, the legs (14) have in peripheral direction (105) at least one recess (143) which extends at least in sections mainly along the central axis (103). These recesses (143) merge into the outer contour (141) of the legs (14) via roundings and/or slopes (1411, 1412, 1421, 1422) or other partial surfaces. It is advantageous if the recesses (143) extend symmetrically from an imaginary center line (144) in peripheral direction (105) and are divided and/or interrupted by slots (12). This results in the legs (14) along the imaginary center line (144) being thicker than the recess areas (143) extending adjacent to the slots (12).

FIGS. 4*a* and 4*b* also show that at the distal end (102) of the fork head (10) the slots (14) form a portion along the central axis (103) which forms a cylindrical outer contour (148) thereby determining a diameter D148, the cylindrical outer contour (148) being interrupted by the recesses (143).

Furthermore, FIGS. 4*a* and 4*b* show that the fork head (10) is U-shaped in side view, and in proximal direction (101) two fork legs (111, 112) with an inner thread (113) are provided, which are suitable to receive a connecting rod (40) therein, and to guide a locking element in the inner thread (113). The two fork legs (111, 112) merge in the central head area via an optional slope (114). A passage opening (18) is provided in the center. It can also be seen that the fork head in its preferred embodiment has one or preferably two laterally arranged recesses (17) which run from proximal (101>102) along, but at a distance from, the central axis (103). These recesses (17) are drain-like or at least partially drain-like, so that an elongated actuating element (72) can at least partially penetrate the fork head (10) to come into contact with the locking ring (20).

Figure 5:
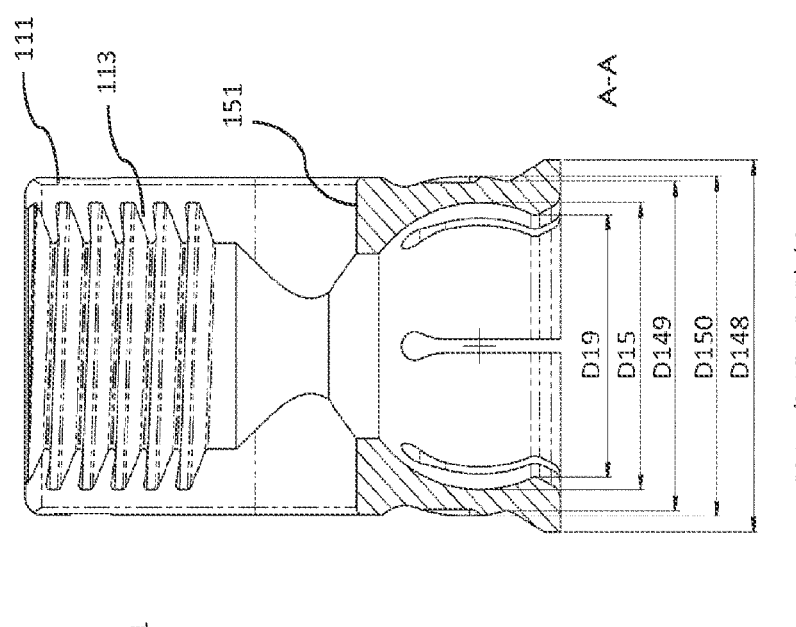
FIG. 5 is the fork head in a side view with a corresponding sectional view.
Figure 5:
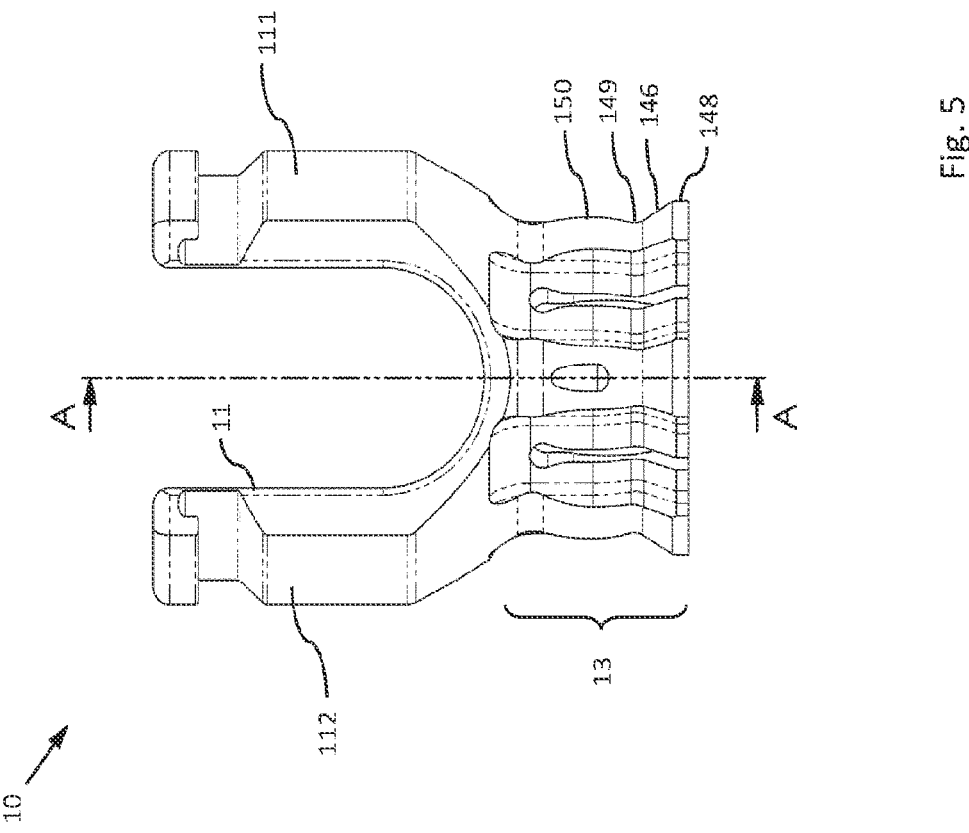

FIG. 5 shows a side view and a cross-section of the fork head (10). From this it can be seen that the fork head (10) has an opening (19) at the distal end (102) with a diameter D19 for a bone anchor (30), and forms a spherical seat (15) with a spherical diameter D15, the diameter D15 being greater than D19, and a minimum deviation (SP1) of the legs (14) must be forced for the bone anchor (30) to be removable or insertable, which is at least half the difference between D15 and D19. The fork head (10) is further characterized in that the spherical head receiving area (13) is proximal (101) to a tapered area (146 to 149) as viewed from the cylindrical portion (148), and the tapered area (146 to 149) is directly or indirectly adjacent to a convexly curved portion of the outer wall (150), thereby deriving diameters D148, D149 and D150, and diameter D148 is greater than D150, and diameter D149 is less than D150 and D148.

Figure 6:
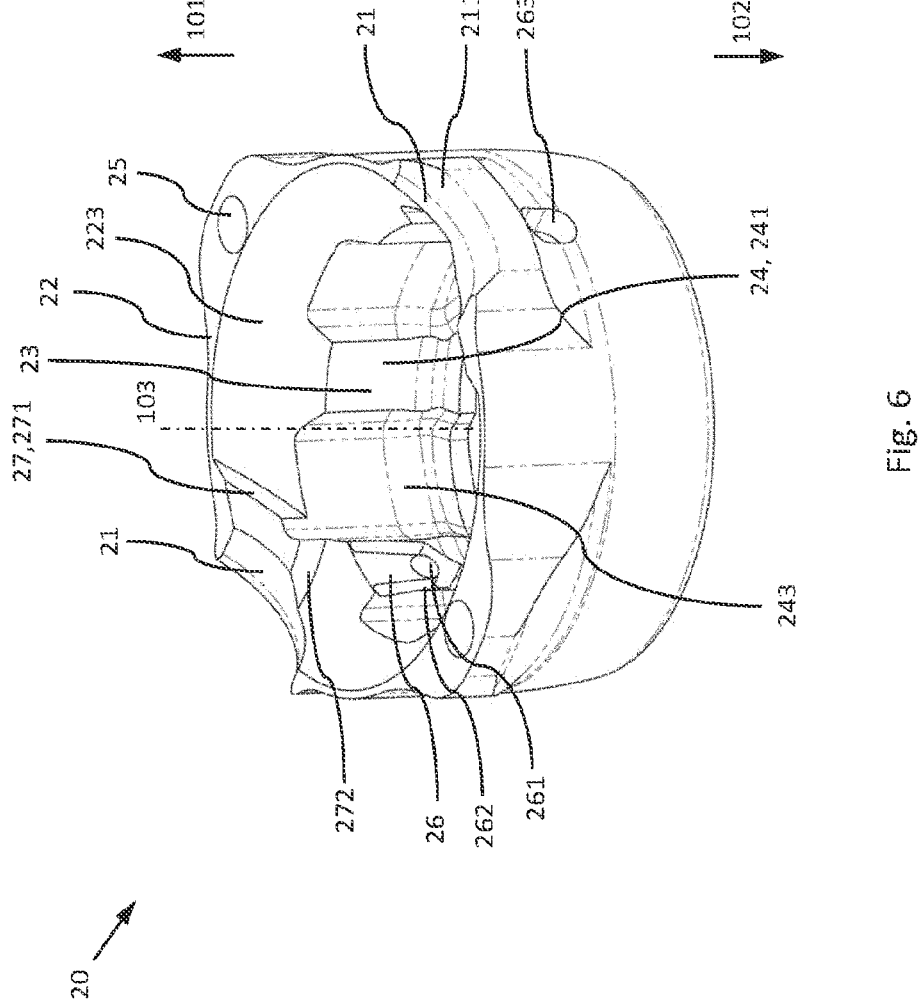
FIG. 6 is the locking ring in an oblique view.

FIG. 6 shows an oblique view of the locking ring. It can be seen that there are two bearing or contact surfaces (21) that are in contact with the connecting rod (40). Preferably, these contact surfaces have a rounding (211) on the radially outer edge. This avoids higher stress concentrations on the connecting rod. The locking ring (20) has a substantially concentric structure, with structures or recesses provided at the edge region for gripping and then rotating the locking ring (20) with the help of instruments. Internally, the locking ring (20) has a central passage opening (23) which, when mounted, engages the spherical head receiving area (13) of the fork head (10). The inner contour is formed by surface elements (24, 241) which are interrupted by recesses (243). The number of surface elements (24, 241) corresponds to the number of legs (14) provided on the fork head (10). The proximal end (22) of the locking ring (20) merges into the central opening via a slope (223). In addition, structures (27) are provided on the locking ring (20) which serve as stops (271, 272). These stops limit the rotatability between the fork head and the locking ring. Furthermore, FIG. 6 shows that spring-type elastic fixing elements (26) are provided on or in the locking ring (20). Preferably, they are configured like a spring tongue (261), which is formed by slots (262) and a cavity (263). In the preferred embodiment, it is shown that the locking ring (20) is provided with at least one contact position or projection (25) at the proximal end (22) so that the locking ring (20) can be actuated from the contact position or projection (25) in addition to the rod support points (21).

Figure 7:
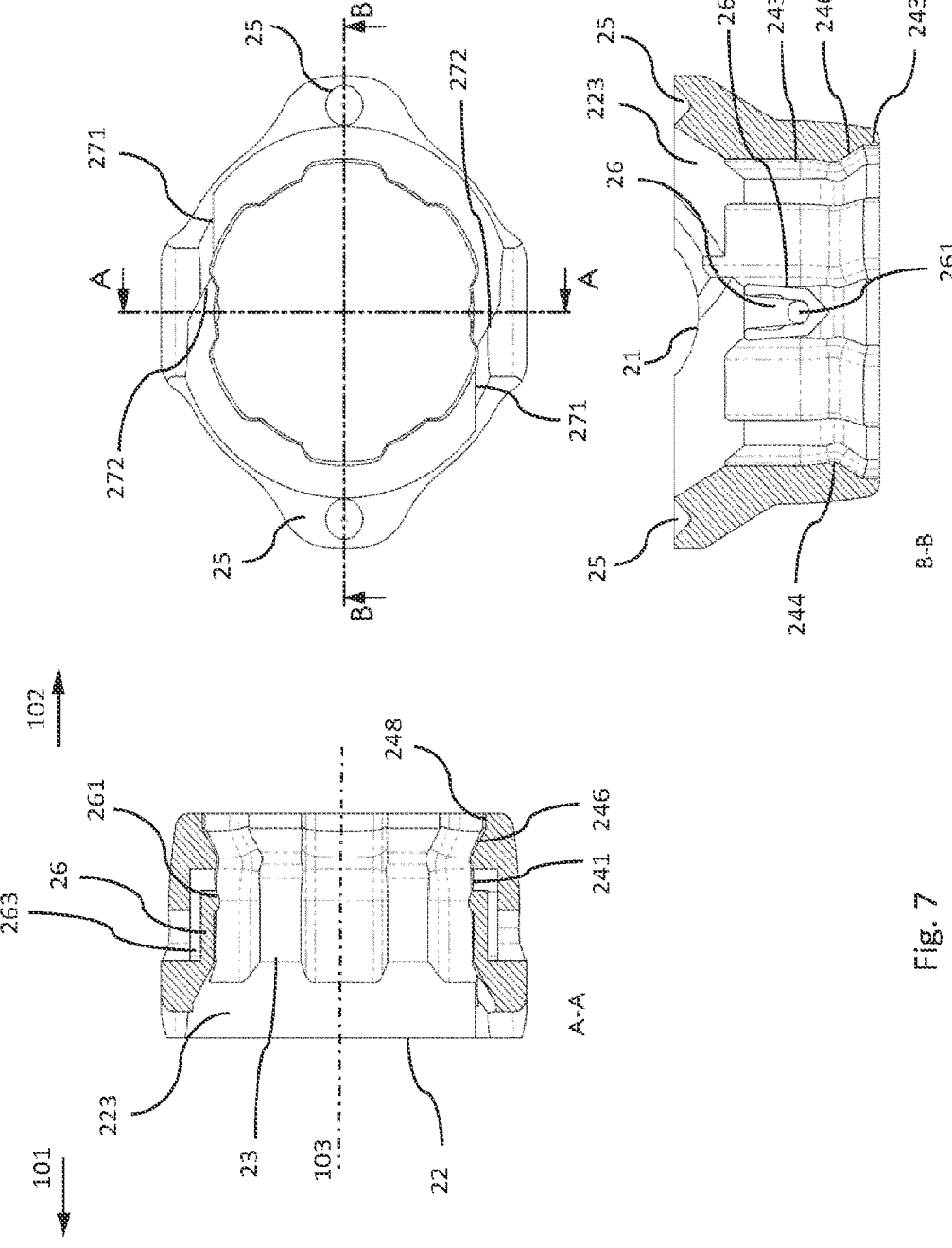
FIG. 7 is the locking ring in a top view with two sectional views.

FIG. 7 shows a top view of the locking ring (20) and two sectional views. Section A-A shows how the fixing elements (26) are configured. It is also shown that at the distal end (102) of the locking ring (20) the inner wall sections (241) form a section along the central axis (103) which forms a cylindrical inner contour (248) with a diameter D248, and this cylindrical inner contour (248) is interrupted by recesses (243). Overall, the inner contour of the locking ring (20) corresponds approximately to a negative imprint of the spherical head receiving area (13) of the fork head (10), but with a slot. FIG. 7 also shows that the stops (271, 272) are arranged in pairs and are effective in two directions.

Figures 8A, 8B, 9A, 9B:
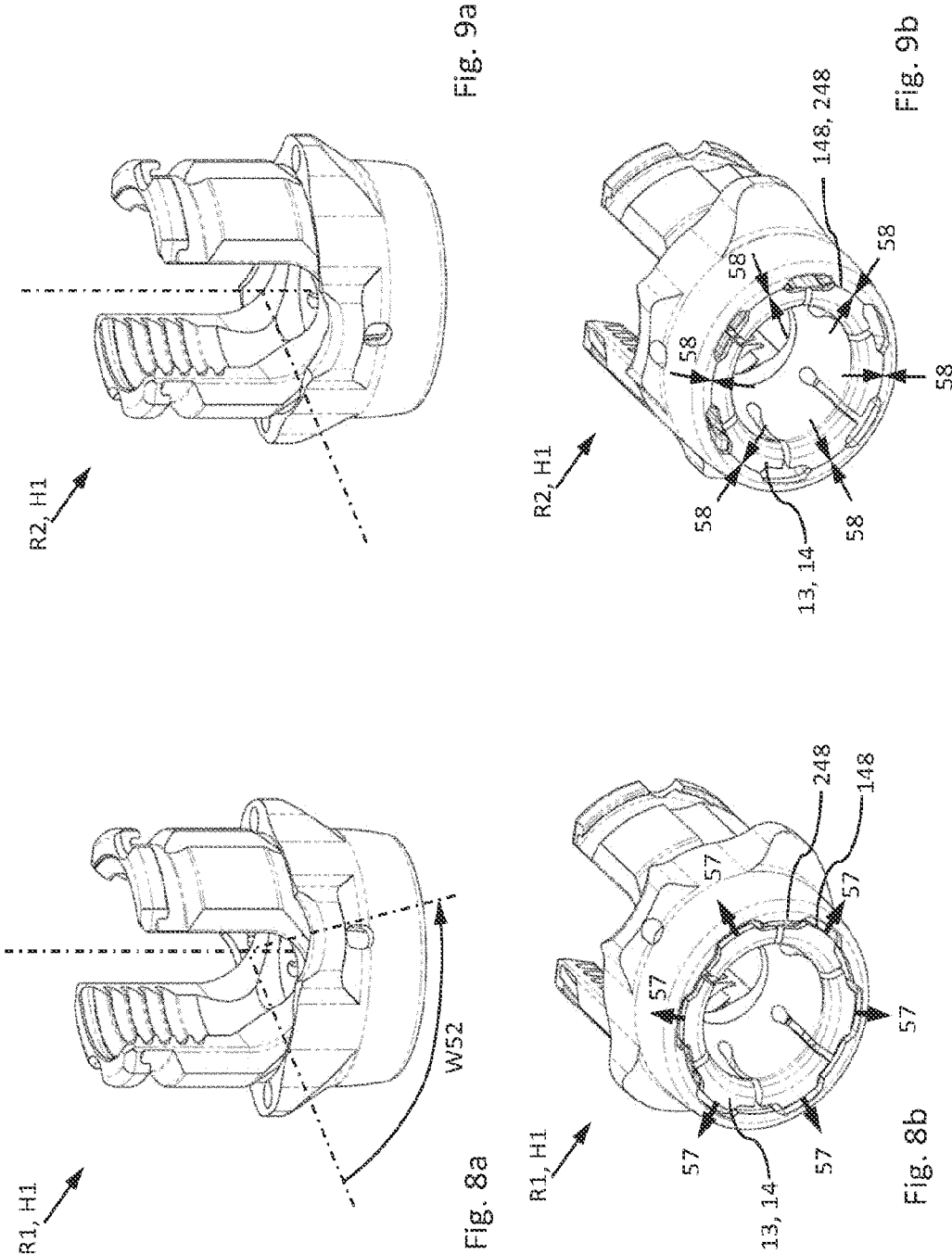
FIGS. 8a and 8b show the fork head with locking ring in a position or rotational position in which a bone anchor can be removed or mounted.
FIGS. 9a and 9b show the fork head with locking ring in a position and rotational position, respectively, in which a bone anchor is held in the spherical head receiving area by a mutual form fit.
Figure 10:
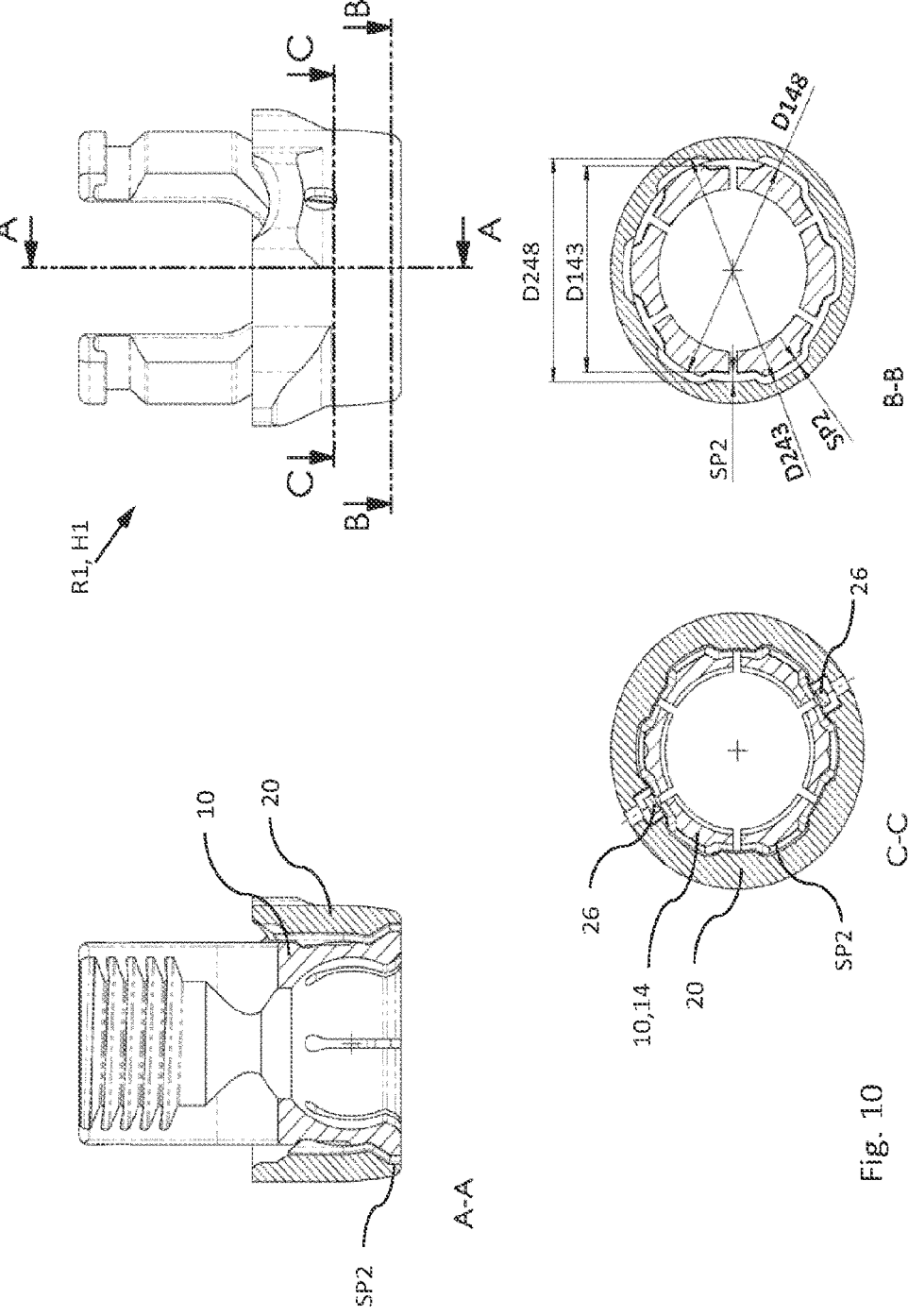
FIG. 10 and FIG. 11 show the fork head and the locking ring in a side view with different sectional views.

In FIGS. 8*a*, 8*b*, 9*a* and 9*b* the functional relationship of the rotation of the locking ring (20) relative to the fork head (10) and the resulting performance is shown. The locking ring (20) is mounted at least partially around the spherical head receiving area (13) so that the locking ring (20) is rotatable about a central axis (103) relative to the fork head (10). A first rotational position (R1) can be set in which the spherical head receiving area (13) can be deflected (57) with its legs (14) radially outwards so that the bone anchor (30) can be removed and/or inserted, and a second rotational position (R2) can be set in which the spherical head receiving area (13) is blocked (58) in its deflectability with its legs (14) so that the bone anchor (30) is held stationary but pivotable. For example, in FIG. 9*b* and FIG. 11 it can be seen that by rotating the locking ring (20) a form fit (58) is provided between the maximum outer cylindrical contour (148) of the fork head (10) and the smallest cylindrical inner contour (248) of the locking ring (20). In FIG. 8*b* and FIG. 10 it is shown that by twisting in another direction the form fit is reopened and the spherical head receiving area (13) is deformable (57). The difference between the first (R1) and second (R2) rotational position can be defined by an angle W52, whereby this angle W52 corresponds approximately to the quotient of 180° divided by the number of legs (14) (FIG. 8*a*).

In FIG. 10 it is also shown that the recesses (143) on the fork head (10) form an outer diameter D143, and the recesses (243) of the locking ring (20) approximate an inner diameter D243, and a diameter configuration (D143, D148, D243 and D248) is established in the rotational position (R1), so that a slot (SP2) is created between the legs (14) of the fork head (10) and the locking ring (20) in the radial direction (104), so that the legs (14) can be deflected (57) radially outwards. The slot (SP2) is dimensioned in such a way that the slot (SP2) is equal to or greater than the minimum deviation (SP1) of the legs (14). This ensures that the bone anchor (30) with its spherical head (31) can be removed or mounted from the spherical seat (15).

Figure 11:
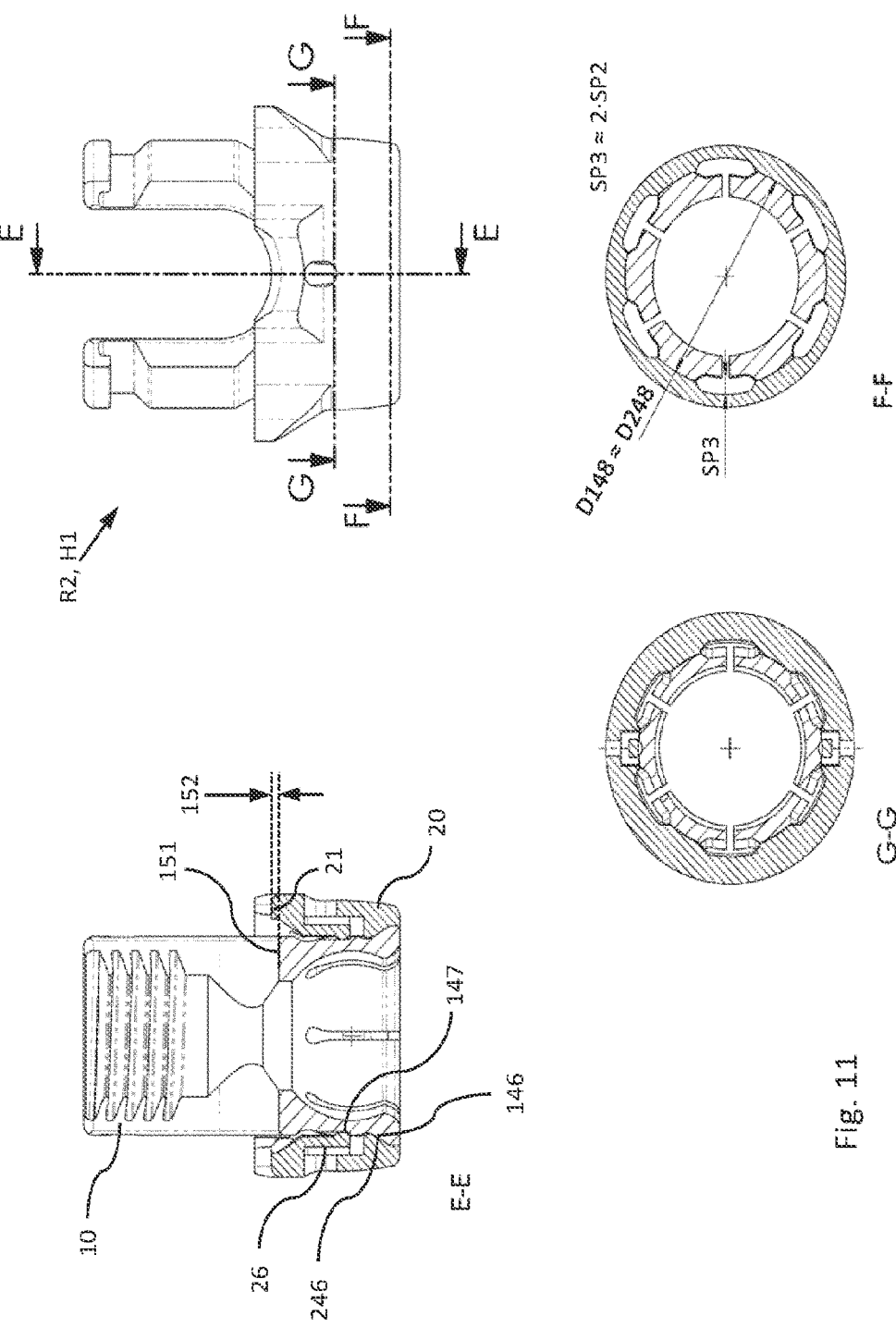

FIG. 11 shows that the aforementioned form fit is determined by the diameters D148 and D248, which are approximately the same size and prevent radial spreading (58) of the legs (14) in the rotational position (R2). By twisting into the rotational position R2, the slot (SP2) is partially or segmentally removed and results in an at least partial form fit, which is interrupted by the recesses (143, 243). In these recess areas (143, 243), the respective slots (SP2) add up to a slot (SP3) approximately twice as large (FIG. 11). Preferably, this form fit is not limited to the cylindrical portion of the spherical head receiving area (13), but also extends to the cone area (146, 246) of both components. By twisting the locking ring (20), an additional form fit is provided between the largest outer conic contour (146) of the fork head (10) and the smallest inner conic contour (246) of the locking ring (20). The form fit is reopened by twisting in a different direction (FIG. 10).

FIG. 11 shows that the locking ring (20) in the rotational position (R2) can take up a first position (R2, H1) along the central axis (103), in which the bone anchor (30) is held stationary but pivotable. If an axial compression force is now transmitted to the locking ring (20) with the help of the connecting rod (40), a second axial position (R2, H2) is taken along the central axis (103). In this position (R2, H2), the spherical head receiving area (13) is compressed by the locking ring (20) in such a way that the bone anchor (30) is held angularly stable in the spherical seat (15). It can be seen that the second axial position (R2, H2) of the locking ring (20) is distal (102) in relation to the first axial position (R2, H1) and the change in position can be determined via a change of displacement (152) of the locking ring (20). The clamping force is mainly generated by a paired arrangement of an inner (246) and outer cone area (146). Here, the axially acting compression force is diverted via the cone angle into a laterally acting and inwardly acting clamping force. FIG. 11 also shows that at least one spring-type elastic fixing element (26) and a stop counter position (147) suitable therefor are formed, which engage with each other as soon as the rotational position (R2) is set, in order to make rotational actuation of the locking ring (20) from this rotational position from R2 to R1 more difficult.

Figures 12A, 12B:
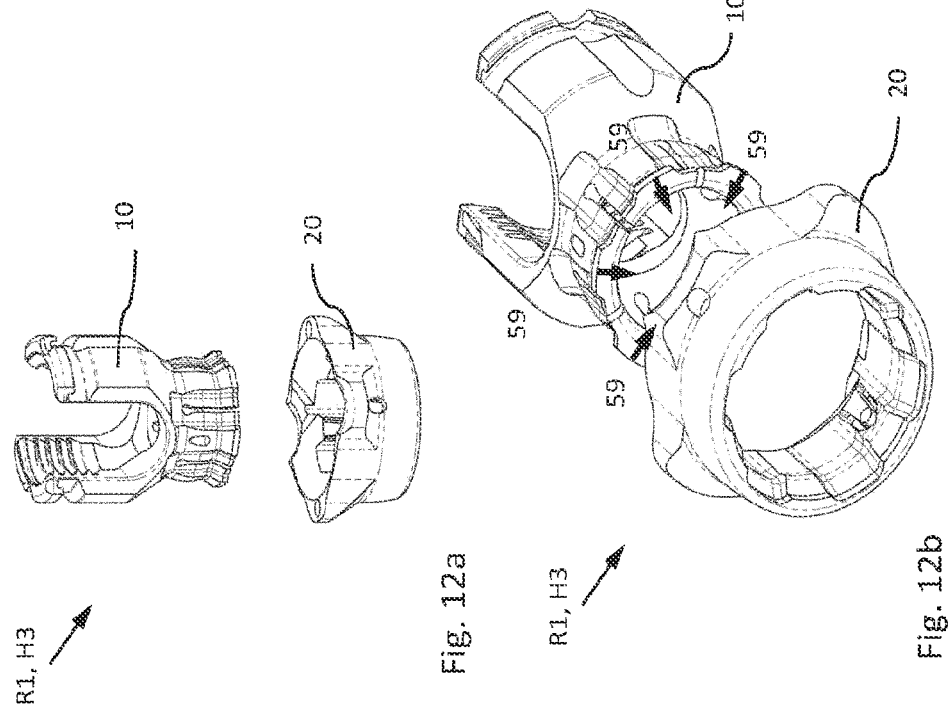
FIGS. 12*a* and 12*b* show the removal of the locking ring from the fork head.

FIGS. 12*a* and 12*b* show the removal of the locking ring (20) from the fork head (10). It is important to note that in the rotational position (R1) the locking ring (20) can take a first position (R1, H1) along the central axis (103) in which the bone anchor (30) can be removed and/or inserted, and as soon as the bone anchor (30) is removed from the spherical head receiving area (13), the locking ring (20) can take another position (R1, H3) along the central axis (103), thereby making the locking ring (20) removable from the fork head (10). It is required that in order to reach the third axial position (R1, H3) along the central axis (103), the spherical head receiving area (13) deflects (59) with its legs (14) radially inwards so that the locking ring (20) can be removed from the fork head (10). For this, the bone anchor (30) must be removed from the spherical head receiving area (13). The axial position (H2) is proximal to the axial position (H3).

Figures 13A, 13B, 13C:
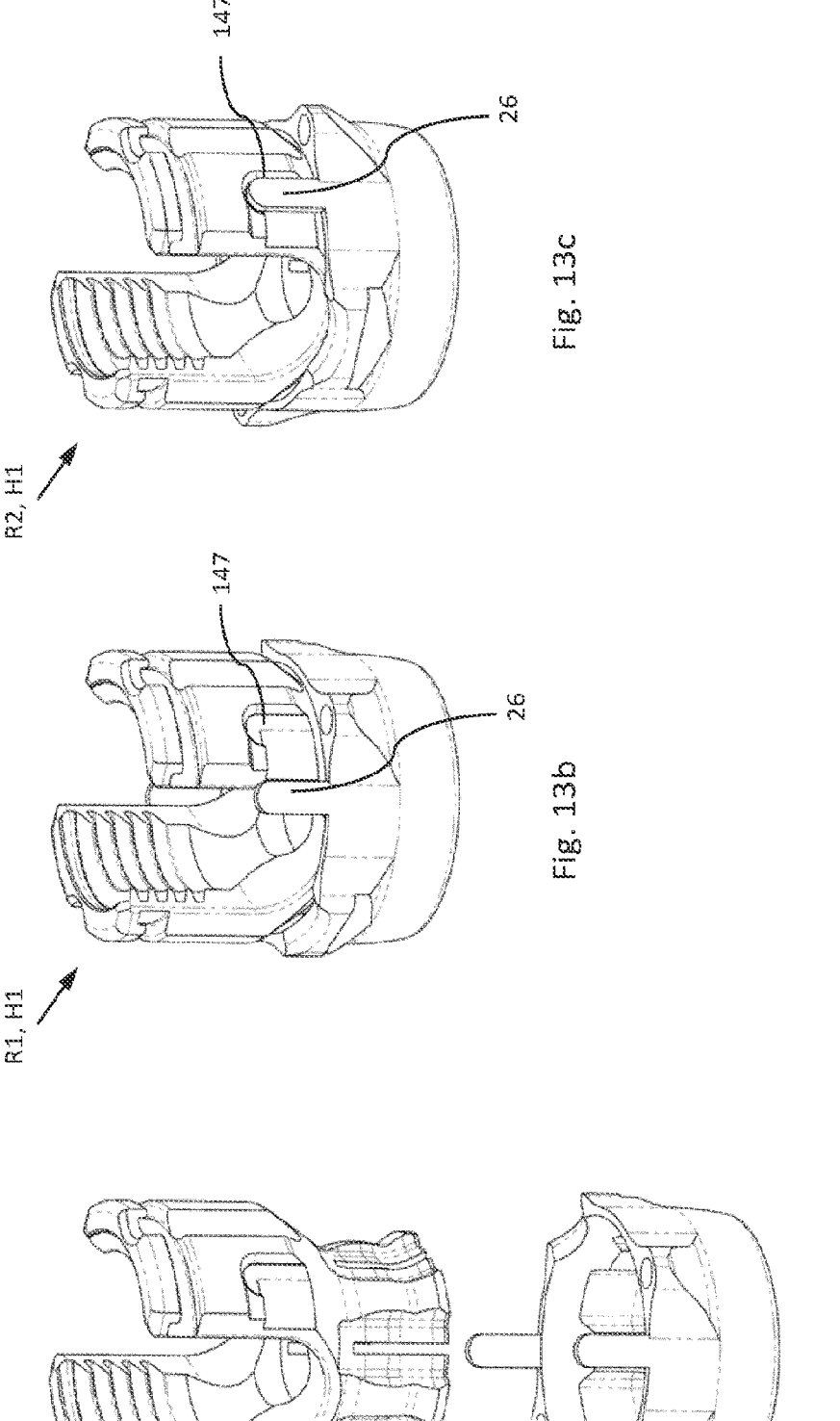
FIGS. 13*a* to 13*c* show an alternative embodiment of the fork head and the locking ring.

FIGS. 13*a* to 13*c* show an alternative design in which the fixing element(s) (26) are arranged at the proximal end of the locking ring (20). For this purpose, a stop counter position (147) is provided on the fork head (10) in the opposite direction as a recessing recess on the fork head, in which the fixing element (26) engages in the rotational position R2. A rotation in the opposite direction, i.e. R1, is thus made more difficult.

Figure 14:
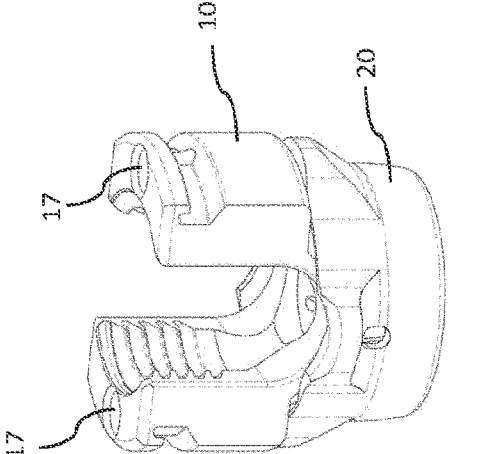
FIG. 14 shows an alternative embodiment.

FIG. 14 shows another alternative embodiment. This embodiment has a closed drain instead of the partial recesses (17) for the use of an instrument (70, 71, 72). It is important that at least one recess or drain (17) is formed in the outer wall of the proximal fork head (10) along but at a distance from the central axis (103), and the recess (17) opens to the contact position or projection (25) of the locking ring (20), so that an actuating element (72) coming from proximally completely penetrates the fork head (10) to reach the contact position or projection (25). This improves the guidance of the actuating element (72).

Figure 15:
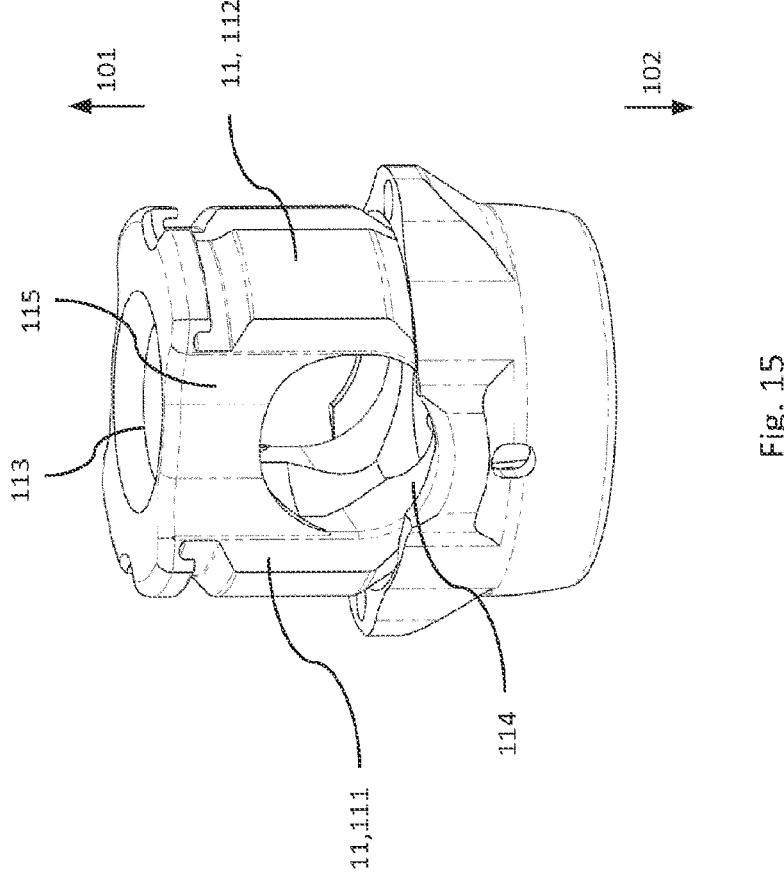
FIG. 15 shows another alternative embodiment with proximally closed fork legs.

FIG. 15 shows another embodiment in which the fork legs (111, 112) are connected (115) to each other at the proximal region (101) and include the internal thread (113) in the assembly. This can be advantageous if the risk of loss of the connecting rod is to be minimized. For example, it can be very advantageous to use a proximally closed fork head (10, 115) for highly loaded bone anchors.

Figures 16A, 16B:
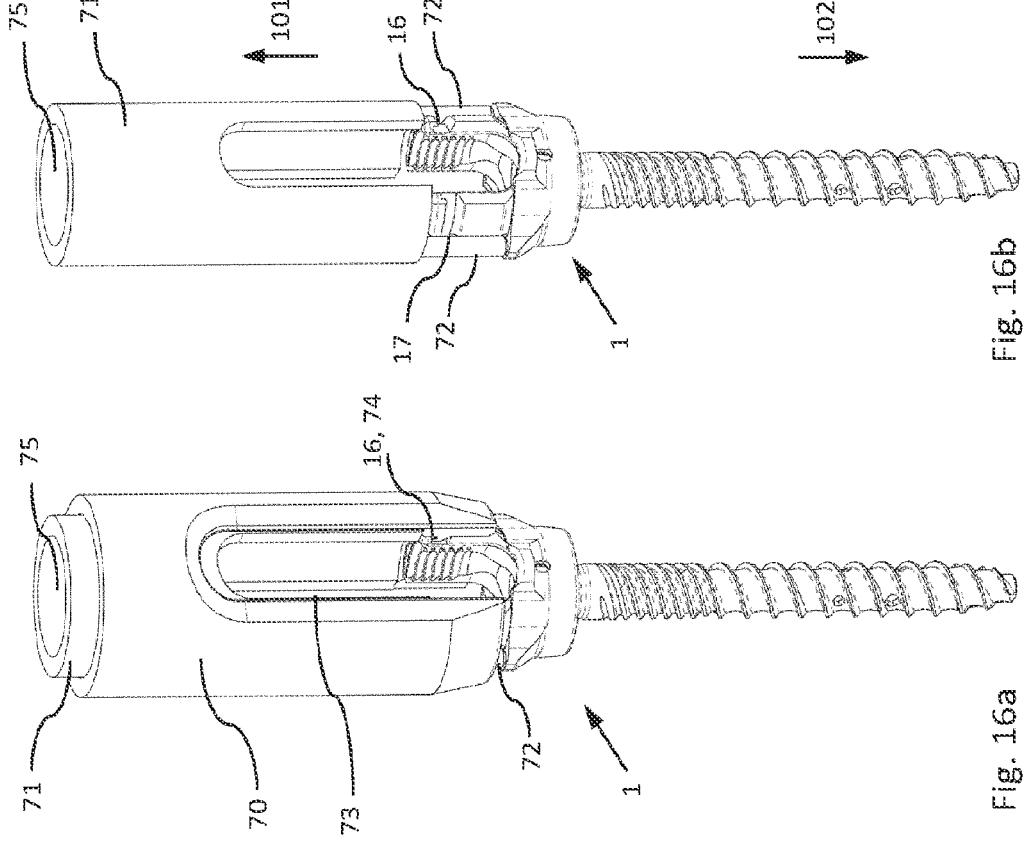
FIGS. 16*a* and 16*b* illustrate the use of an instrument for temporary fixation.

According to the preferred embodiment, at least one additional projection or contact position (25), which is indirectly or directly an element of the outer wall of the locking ring (20) and through which a compression force can be introduced, provides a possibility to achieve the clamping of the bone anchor head (31) even without an inserted connecting rod (40) and/or grub screw (60) (FIGS. 16*a* and 16*b*). For this purpose, as already mentioned, at least one contact position or projection (25) is provided on the proximal outer wall (22) of the locking ring (20), and at least one retaining feature (16) is additionally provided on the proximal fork head (10) for the attachment of an instrument (70, 71). Optionally, a recess (17) is provided on the fork head so that the contact position (25) is accessible for an instrument from proximally (101). A suitable instrument (70, 71) can be used to apply a compressive force to the contact position (25), with the retaining feature (16) serving as a counter-bearing for the reaction tensile force (FIGS. 16*a* and 16*b*). In order to initiate a relative movement, the instrument must comprise at least two sleeves (70, 71) which are arranged so as to be displaceable relative to one another. Suitable for this purpose is an outer sleeve (70), which can be attached to the retaining feature (16) of the fork head (10) by a suitable engagement feature (74), and an inner sleeve (71), which has corresponding cones or projections (72), which communicates directly with the contact position (25) and can apply a compressive force. In FIG. 16*b*, the outer instrument sleeve (70) is hidden so that the cones (72) are more visible. These cones or protrusions (72) actuate the locking ring (20) proximally and at least partially penetrate the fork head (10). Preferably, such an instrument has a lateral oval cut-out (73) into which a connecting rod (40) can be inserted and guided. When a pressure force is applied to the contact position (25), a stable-angle clamping of the bone anchor (30) in the fork head (10, 13) is created without the need for a connecting rod (40) and/or grub screw (60). A central opening (75) is located centrally in the instrument (70, 71) for the transport of a further sleeve and/or grub screw (60).

The invention claimed is:

1. An osteosynthesis device for treating the spine, comprising:
a fork head which is U-shaped in a side view, has two fork legs in a proximal direction with an internal thread, and in which a connecting rod can be received, and a locking element is guided in the internal thread, and
wherein the fork head has a spherical head receiving area and is detachably connected to a bone anchor, and the bone anchor is pivotably mounted in a spherical seat of the spherical head receiving area,
wherein the fork head has slots which are open in the distal direction at the spherical head receiving area and at least two deflectable legs are thereby formed; and a locking ring mounted at least partially around the spherical head receiving area, wherein the locking ring is rotatable about a central axis relative to the fork head, and
a first rotational position (R1) can be set in which the spherical head receiving area can be deflected with its legs radially outwards, so that the bone anchor can be removed and/or inserted, and a second rotational position (R2) can be set, in which the spherical head receiving area with its legs is blocked in its deflectability,
wherein the legs form an outer contour of the spherical head receiving area,
wherein the legs in peripheral direction have at least one recess extending at least in sections mainly along the central axis and a distal end of the locking ring inner wall sections form a section along the central axis which forms a cylindrical inner contour with a diameter D248,
wherein the cylindrical inner contour is interrupted in circumferential direction by at least one recess,
wherein, in a second rotational position (R2) a maximum outer cylinder contour of the spherical head receiving area of the fork head and a smallest inner cylinder contour of the locking ring provides a form fit, and wherein a cone area for the fork head and a cone area of the locking ring provide the form fit so that the bone anchor is held fixed but pivotable.

2. The osteosynthesis device according to claim 1, wherein the locking ring in the rotational position (R2) can take a first position (R2, H1) along the central axis, in which the bone anchor is held fixed but pivotable, and a second position (R2, H2) along the central axis, in which position (R2, H2) the spherical head receiving area is compressed by the locking ring in such a way that the bone anchor is held in the spherical seat in an angularly stable manner.

3. The osteosynthesis device according to claim 2, wherein the second axial position (R2, H2) of the locking ring is distal with respect to the first axial position (R2, H1) and the change in position can be determined via a change of displacement of the locking ring.

4. The osteosynthesis device according to claim 1, wherein the locking ring in a rotational position can take a first position (R1, H1) along the central axis, in which the bone anchor is removable and/or insertable, and the locking ring can take a third position (R1, H3) along the central axis, and thereby the locking ring is removable from the fork head.

5. The osteosynthesis device according to claim 4, wherein only when the bone anchor is removed from the spherical head receiving area, in order to reach the third position (R1, H3) along the central axis, the spherical head receiving area deflects with its legs radially inwards so that the locking ring can be removed from the fork head.

6. The osteosynthesis device according to claim 1, wherein the axial position H1 is substantially the same for both rotational positions (R1 and R2).

7. The osteosynthesis device according to claim 1, wherein the axial position (H2) is proximal to the axial position (H3).

8. The osteosynthesis device according to claim 1, wherein the difference between the first (R1) and second (R2) rotational position is determinable by an angle W52, said angle W52 being substantially equal to the quotient of 180° divided by the number of legs.

9. The osteosynthesis device according to claim 1, wherein at least one of the rotational positions (R1, R2) is limited in rotation between the locking ring and the fork head by a stop.

10. The osteosynthesis device according to claim 1, wherein the at least one recess is a plurality of recesses, and wherein the plurality of recesses merge into the outer contour of the legs via roundings and/or slopes or other partial surfaces.

11. The osteosynthesis device according to claim 1, wherein the at least one recess is a plurality of recesses, and wherein the plurality of recesses are symmetrically from an imaginary center line in peripheral direction.

12. The osteosynthesis device according to claim 1, wherein the at least one recess is a plurality of recesses, and wherein the plurality of recesses are divided and/or interrupted by slots.

13. The osteosynthesis device according to claim 1, wherein the legs along the imaginary center line are thicker than the regions adjacent to the slot.

14. The osteosynthesis device according to claim 1, wherein the distal end of the fork head the slots form a section along the central axis which forms a cylindrical outer contour and thereby determines a diameter D148, wherein at least one recess is a plurality of recesses, and the cylindrical outer contour is interrupted by the plurality of the recesses.

15. The osteosynthesis device according to claim 14, wherein the diameters D148 and D248 are substantially equal and prevent radial spreading of the legs in the rotational position (R2).

16. The osteosynthesis device according to claim 14, wherein the plurality of the recesses on the fork head form an outer diameter D143, and the plurality of the recesses of the locking ring approximate an inner diameter D243, and a diameter configuration (D143, D148, D243 and D248) is established in the rotational position (R1), so that in radial direction a slot (SP2) is provided between the legs of the fork head and the locking ring, so that the legs can be deflected radially outwards.

17. The osteosynthesis device according to claim 1, wherein the fork head has at the distal end an opening with diameter D19 for a bone anchor, and forms a spherical seat with a spherical diameter D15, wherein the diameter D15 is greater than D19, and a minimum deviation (SP1) of the legs must be forced for the bone anchor to be removable or insertable which is at least half the difference of D15 and D19.

18. The osteosynthesis device according to claim 1, wherein the slot (SP2) is equal to or greater than the dimension of a minimum deviation of the legs (SP1).

19. The osteosynthesis device according to claim 1, wherein at least one spring-type elastic fixing element and a stop counter position suitable therefor are formed on or in the locking ring, which are engaged with each other once the rotational position (R2) is set, in order to impede rotational actuation of the locking ring from R2 to R1.

20. The osteosynthesis device according to claim 1, wherein the spherical head receiving area, viewed proximally from a cylindrical portion, adjoins a tapered area, which is directly or indirectly adjacent to a convexly curved portion of the outer wall, thereby allowing the diameters D148, D149 and D150 to be determined, and the diameter D148 is larger than D150, and the diameter D149 is smaller than D150 and D148.

21. The osteosynthesis device according to claim 1, wherein at least one contact position or projection is provided on the locking ring directed in the proximal direction, and at least one retaining feature is provided on the proximal fork head for the attachment of an instrument, and if a compressive force is applied between the retaining feature and the contact position, the bone anchor is clamped in the fork head in an angularly stable manner without a connecting rod and/or locking element being present.

22. The osteosynthesis device according to claim 1, wherein at least one recess or drain is formed in the outer wall of the proximal fork head along but at a distance from the central axis, and the at least one recess opens to a contact position or projection of the locking ring, so that an actuating element coming from proximal penetrates the fork head at least partially to reach the contact position or projection.

23. The osteosynthesis device according to claim 1, wherein the deflectable legs coming from distally join above the spherical seat and form a middle fork head area and the fork legs.

24. The osteosynthesis device according to claim 1, wherein the fork legs are coupled to each other at a proximal region and include the internal thread in the assembly.

25. The osteosynthesis device according to claim 1, wherein the fork head and/or the locking ring is manufactured by an additive manufacturing process and consists of a metallic alloy, such as a titanium alloy, cobalt-chromium or stainless steel alloy.

26. The osteosynthesis device according to claim 1, wherein a form fit between a maximum outer cylindrical contour of the fork head and a smallest inner cylindrical contour of the locking ring is provided by twisting the locking ring.

27. The osteosynthesis device according to claim 26, wherein the form fit is reopened by twisting in another direction.

28. The osteosynthesis device according to claim 1, wherein a form fit is provided between a largest outer conic contour of the fork head and a smallest inner conic contour of the locking ring by twisting the locking ring.

29. An osteosynthesis device for treating the spine, comprising:

a fork head which is U-shaped in a side view, has two fork legs in a proximal direction with an internal thread, and in which a connecting rod can be received, and a locking element is guided in the internal thread, and wherein the fork head has a spherical head receiving area and is detachably connected to a bone anchor, and the bone anchor is pivotably mounted in a spherical seat of the spherical head receiving area, wherein the fork head has slots which are open in the distal direction at the spherical head receiving area and at least two deflectable legs are thereby formed; and a locking ring mounted at least partially around the spherical head receiving area, wherein the locking ring is rotatable about a central axis relative to the fork head, and a first rotational position (R1) can be set in which the spherical head receiving area can be deflected with its legs radially outwards, so that the bone anchor can be removed and/or inserted, and a second rotational position (R2) can be set, in which the spherical head receiving area with its legs is blocked in its deflectability, wherein the legs form an outer contour of the spherical head receiving area, wherein the legs in peripheral direction have at least one recess extending at least in sections mainly along the central axis and a distal end of the locking ring inner wall sections form a section along the central axis which forms a cylindrical inner contour with a diameter D248, wherein the cylindrical inner contour is interrupted in circumferential direction by at least one recess, wherein, in a second rotational position (R2) a maximum outer cylinder contour of the spherical head receiving area of the fork head and a smallest inner cylinder contour of the locking ring provides a form fit, so that the bone anchor is held fixed but pivotable, and wherein the difference between the first (R1) and second (R2) rotational position can be defined by an angle corresponding approximately to the quotient of 180° divided by the number of legs.

\* \* \* \* \*